(12) United States Patent
Sherman et al.

(10) Patent No.: US 11,832,964 B2
(45) Date of Patent: Dec. 5, 2023

(54) TECHNOLOGIES FOR MONITORING BONE INGROWTH OF AN ORTHOPAEDIC PROSTHESIS

(71) Applicant: DePuy Synthes Products, Inc., Raynham, MA (US)

(72) Inventors: Jason T. Sherman, Warsaw, IN (US); Daniel D. Auger, Fort Wayne, IN (US)

(73) Assignee: Depuy Synthes Products, Inc., Raynham, MA (US)

( * ) Notice: Subject to any disclaimer, the term of this patent is extended or adjusted under 35 U.S.C. 154(b) by 792 days.

(21) Appl. No.: 16/836,614

(22) Filed: Mar. 31, 2020

(65) Prior Publication Data

US 2021/0298668 A1  Sep. 30, 2021

(51) Int. Cl.
*A61F 2/38* (2006.01)
*A61B 5/00* (2006.01)
*A61F 2/30* (2006.01)
*A61F 2/46* (2006.01)

(52) U.S. Cl.
CPC ............ *A61B 5/4851* (2013.01); *A61F 2/389* (2013.01); *A61F 2/3859* (2013.01); *A61F 2002/3069* (2013.01); *A61F 2002/3093* (2013.01); *A61F 2002/30784* (2013.01); *A61F 2002/4666* (2013.01)

(58) Field of Classification Search
CPC .......... A61F 2/389; A61F 2/3859; A61F 2/40; A61F 2/32; A61F 2/36; A61F 2/28; A61B 5/4851
See application file for complete search history.

(56) References Cited

U.S. PATENT DOCUMENTS

| | | |
|---|---|---|
| 5,197,488 A | 3/1993 | Kovacevic |
| 8,075,627 B2 | 12/2011 | Caylor, III et al. |
| 8,176,922 B2 | 5/2012 | Sherman et al. |
| 2003/0040806 A1 | 2/2003 | MacDonald |
| 2004/0019384 A1 | 1/2004 | Kirking |
| 2018/0161168 A1 | 6/2018 | Johannaber |

FOREIGN PATENT DOCUMENTS

EP  2783659 A1  10/2014

OTHER PUBLICATIONS

International Search Report for International Application No. PCT/IB2021/050718; received Apr. 28, 2021; 8 pages.

*Primary Examiner* — Jason-Dennis N Stewart
(74) *Attorney, Agent, or Firm* — BARNES & THORNBURG LLP

(57) ABSTRACT

A system for monitoring bone ingrowth includes an orthopaedic prosthesis having a circuit configured to transmit force sensor data indicative of an amount of force applied to a stem of the orthopaedic prosthesis in response to receiving power from an external power supply. The force sensor data is indicative of bone ingrowth of the orthopaedic prosthesis. As such, an orthopaedic surgeon may monitored the force sensor data over time to ensure bone ingrowth of the orthopaedic prosthesis has sufficiently occurred.

16 Claims, 12 Drawing Sheets

TECHNOLOGIES FOR MONITORING BONE INGROWTH OF AN ORTHOPAEDIC PROSTHESIS

TECHNICAL FIELD

The present disclosure relates generally to technologies for monitoring the securement of an orthopaedic prosthesis in a patient and, more particularly, to an orthopaedic prosthesis and associated system for monitoring bone ingrowth of the orthopaedic prosthesis.

BACKGROUND

Joint arthroplasty is a well-known surgical procedure by which a diseased and/or damaged natural joint is replaced by a prosthetic joint, which may include one or more orthopaedic prostheses. For example, in a knee arthroplasty surgical procedure, a patient's natural knee joint is partially or totally replaced by a prosthetic knee joint. Similarly, in a hip arthroplasty surgical procedure, a patient's natural hip ball and socket joint is partially or totally replaced by a prosthetic hip joint.

One type of orthopaedic prostheses that may be used to replace a patient's joint are known as cementless orthopaedic prostheses. An orthopaedic surgeon implants cementless prostheses into a patient's boney anatomy by impacting the prosthesis into a corresponding bone of the patient using an orthopaedic prosthesis inserter or other suitable instrument. Cementless orthopaedic prostheses include a porous-metal coating on their exterior to facilitate bone ingrowth into the cementless orthopaedic prostheses. Long term securement and stability of a cementless orthopaedic prosthesis is dependent on sufficient bone ingrowth. Poor bone ingrowth into a cementless orthopaedic prosthesis can result is loosening of the prosthesis and may require revision surgery to correct such loosening.

SUMMARY

According to an aspect of the present disclosure, an orthopaedic prosthesis for monitoring bone ingrowth includes a stem configured to be implanted into a medullary canal of a bone of a patient and a porous-metal coating coupled to an external surface of the stem. The porous-metal coating is configured to facilitate ingrowth of the bone of the patient while the orthopaedic prosthesis is implanted into the bone of the patient. The orthopedic prosthesis also includes a securement monitoring circuit that includes a force sensor coupled to the stem of the orthopaedic prosthesis and positioned underneath the porous-metal coating. The force sensor may be configured to produce force sensor data indicative of an amount of force applied to the stem of the orthopaedic prosthesis, and the amount of force applied to the stem may be dependent on bone ingrowth of the orthopaedic prosthesis. The securement monitoring circuit may also include a communication circuit configured to transmit the force sensor data to an external data communication device.

In some embodiments, the orthopaedic prosthesis is embodied as a tibial component including a tibial tray and the stem. In such embodiments, the stem may include a proximal end coupled to the tibial tray and a distal tip opposite the proximal end. In some embodiments, the force sensor may be embodied as an annular force sensor coupled to the stem between the proximal end and the distal tip. In other embodiments, the annular force sensor may be shaped to form a distal tip of the stem opposite the proximal end. Additionally, in other embodiments, the annular force sensor may be embedded in an perimeter lip of an inferior side of the tibial tray.

In some embodiments, the orthopaedic prosthesis may be embodied as a femoral component and the stem may include a proximal end and a distal tip opposite the proximal end. In such embodiments, the force sensor may be embodied as annular force sensor coupled to the stem between the proximal end and the distal tip. In other embodiments, the force sensor may be shaped to form the distal tip of the stem opposite the proximal end.

Additionally, in some embodiments, the orthopaedic prosthesis may be embodied as a humeral component and the stem may include a proximal end and a distal tip opposite the proximal end. In such embodiments, the force sensor may be embodied as annular force sensor coupled to the stem between the proximal end and the distal tip. In other embodiments, the force sensor may be shaped to form the distal tip of the stem opposite the proximal end.

In some embodiments, the force sensor may be embodied as a 3-axis force sensor. Additionally or alternatively, the force sensor may be embodied as a piezoelectric sensor. Additionally, in some embodiments, the securement monitoring circuit may further include a power circuit to provide power to other electrical components of the securement monitoring circuit. In such embodiments, the power circuit may be configured to receive power from a power supply external from the orthopaedic prosthesis. Further, in some embodiments, the securement monitoring circuit may also include processing circuitry configured to receive the force sensor data from the force sensor and store the force sensor data in a local memory along with historical force sensor data. In such embodiments, the communication circuit may be configured to transmit the force sensor data and the historical force sensor data as a batch of force sensor data to the external data communication device.

According to another aspect, a system for monitoring bone ingrowth of an orthopaedic prosthesis includes an orthopaedic prosthesis and an external data communication device. The orthopaedic prosthesis may include a stem configured to be implanted into a medullary canal of a bone of a patient and a porous-metal coating coupled to an external surface of the stem. The porous-metal coating may be configured to facilitate ingrowth of the bone of the patient while the orthopaedic prosthesis is implanted into the bone of the patient. The orthopaedic prosthesis may also include a securement monitoring circuit. The securement monitoring circuit may include a force sensor and a communication circuit. The force sensor may be coupled to the stem of the orthopaedic prosthesis and positioned underneath the porous-metal coating. Additionally, the force sensor may be configured to produce force sensor data indicative of an amount of force applied to the stem of the orthopaedic prosthesis, and the amount of force applied to the stem may be dependent on bone ingrowth of the orthopaedic prosthesis. The communication circuit may be configured to transmit the force sensor data to an external data communication device.

The external data communication device may include a communication circuit and processing circuitry. The communication circuit may be configured to communicate with the communication circuit of the orthopaedic prosthesis to receive the force sensor data. The processing circuitry may be configured to generate, based on the force sensor data, an output on an output device indicative of the bone ingrowth of the orthopaedic prosthesis.

In some embodiments, the orthopaedic prosthesis is embodied as a tibial component including a tibial tray and the stem. In such embodiments, the stem may include a proximal end coupled to the tibial tray and a distal tip opposite the proximal end. In some embodiments, the force sensor may be embodied as an annular force sensor coupled to the stem between the proximal end and the distal tip. In other embodiments, the annular force sensor may be shaped to form a distal tip of the stem opposite the proximal end. Additionally, in other embodiments, the annular force sensor may be embedded in an perimeter lip of an inferior side of the tibial tray.

In some embodiments, the orthopaedic prosthesis may be embodied as a femoral component and the stem may include a proximal end and a distal tip opposite the proximal end. In such embodiments, the force sensor may be embodied as annular force sensor coupled to the stem between the proximal end and the distal tip. In other embodiments, the force sensor may be shaped to form the distal tip of the stem opposite the proximal end.

Additionally, in some embodiments, the orthopaedic prosthesis may be embodied as a humeral component and the stem may include a proximal end and a distal tip opposite the proximal end. In such embodiments, the force sensor may be embodied as annular force sensor coupled to the stem between the proximal end and the distal tip. In other embodiments, the force sensor may be shaped to form the distal tip of the stem opposite the proximal end.

In some embodiments, the force sensor may be embodied as a 3-axis force sensor. Additionally or alternatively, the force sensor may be embodied as a piezoelectric sensor. Additionally, in some embodiments, the system may further include an external power supply. In such embodiments, the securement monitoring circuit may further include a power circuit to provide power to other electrical components of the securement monitoring circuit. The external power supply may be configured to provide power to the power circuit of the securement monitoring circuit while the orthopaedic prosthesis is implanted into the bone of the patient.

Accordingly to a further aspect, a surgical method for monitoring bone ingrowth of an orthopaedic prosthesis may include implanting a cementless orthopaedic prosthesis in a patient including inserting a stem of the cementless orthopaedic prosthesis into a medullary canal of a patient. The cementless orthopaedic prosthesis may include a securement monitoring circuit configured to produce force sensor data indicative of an amount of force applied to the stem of the cementless orthopaedic prosthesis, and the amount of force applied to the stem is dependent on bone ingrowth of the orthopaedic prosthesis. The method may also include performing a post-op examination of the patient including providing power to the securement monitoring circuit of the orthopaedic prosthesis subsequent to implanting the cementless orthopaedic prosthesis to cause the securement monitoring circuit to transmit the force sensor data while the patient performs an activity of daily living; and analyzing the force sensor data to determine whether the bone ingrowth of the cementless orthopaedic prosthesis is sufficient.

In some embodiments, the surgical method may further include performing a subsequent post-op examination of the patient, which may include providing power to the securement monitoring circuit of the orthopaedic prosthesis subsequent to implanting the cementless orthopaedic prosthesis to cause the securement monitoring circuit to transmit additional force sensor data while the patient performs an activity of daily living. Analyzing the force sensor data may include comparing the force sensor data and the additional force sensor data. In some embodiments, analyzing the force sensor data may include determining bone ingrowth is sufficient based on a comparison of the force sensor data and a reference threshold value. Additionally, in some embodiments, the surgical method may further include performing a revision surgery on the cementless orthopaedic prosthesis in response to a determination that the bone ingrowth of the cementless orthopaedic prosthesis is not sufficient.

BRIEF DESCRIPTION OF THE DRAWINGS

The concepts described herein are illustrated by way of example and not by way of limitation in the accompanying figures. For simplicity and clarity of illustration, elements illustrated in the figures are not necessarily drawn to scale. Where considered appropriate, reference labels have been repeated among the figures to indicate corresponding or analogous elements. The detailed description particularly refers to the accompanying figures in which.

DETAILED DESCRIPTION OF THE DRAWINGS

Figure 1:
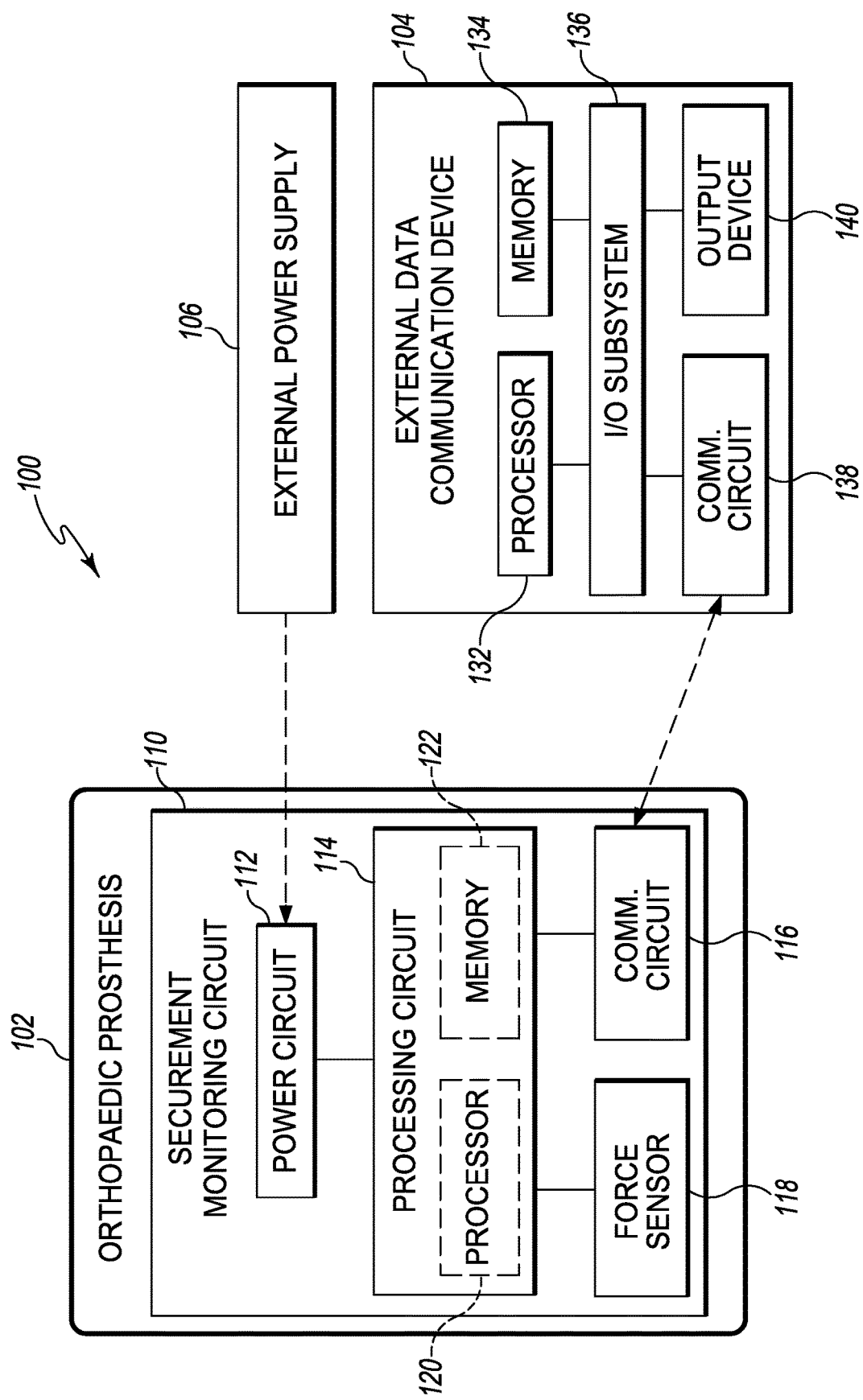
FIG. 1 is a block diagram of a system for monitoring bone ingrowth of an orthopaedic prosthesis.
Figure 2:
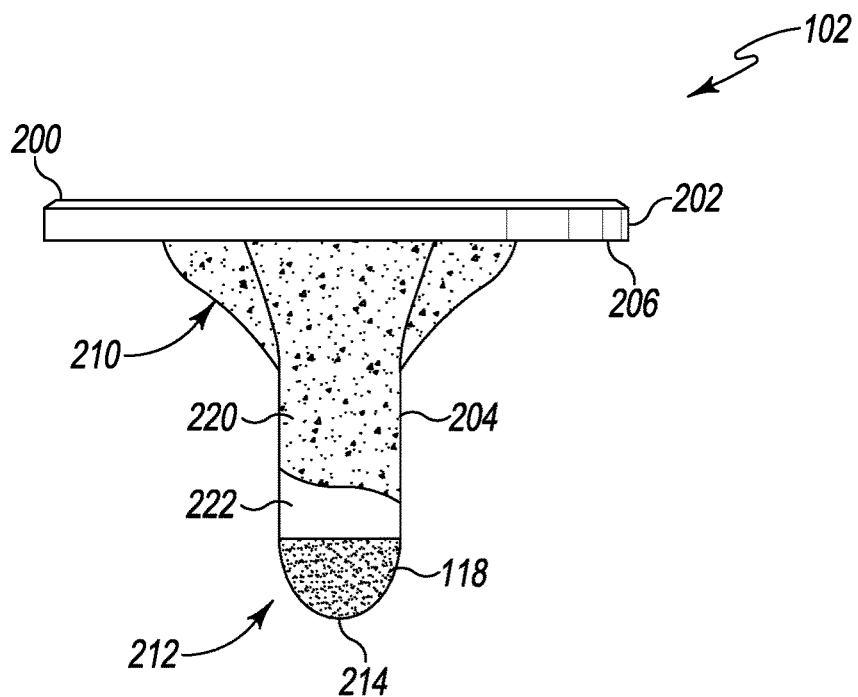
FIG. 2 is an elevation view of the orthopaedic prosthesis of FIG. 1 embodied as a tibial knee component having a force sensor incorporated therewith.

While the concepts of the present disclosure are susceptible to various modifications and alternative forms, specific embodiments thereof have been shown by way of example in the drawings and will be described herein in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

Terms representing anatomical references, such as anterior, posterior, medial, lateral, superior, inferior, etcetera, may be used throughout the specification in reference to the orthopaedic implants or prostheses and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described. Additionally, it should be appreciated that items included in a list in the form of "at least one A, B, and C" can mean (A); (B); (C); (A and B); (A and C); (B and C); or (A, B, and C). Similarly, items listed in the form of "at least one of A, B, or C" can mean (A); (B); (C); (A and B); (A and C); (B and C); or (A, B, and C).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features.

Referring now to FIG. 1, an illustrative orthopaedic prosthesis system 100 includes an orthopaedic prosthesis 102, an external data communication device 104, and, optionally, an external power supply 106. As discussed in more detail below, the orthopaedic prosthesis 102 is configured to be implanted into a bone of a patient to replace a partial joint of the patient. To do so, an orthopaedic surgeon may perform an orthopaedic surgical procedure in which a stem of the orthopaedic prosthesis 102 is inserted into a surgically-prepared medullary canal of the patient, depending on which joint is being replaced. The illustrative orthopaedic prosthesis 102 is a cementless orthopaedic prosthesis 102 and includes a porous-metal coating to facilitate bone ingrowth of the orthopaedic prosthesis 102 to properly secure the orthopaedic prosthesis 102 to the patient's bony anatomy.

In use, as discussed in more detail below, the orthopaedic prosthesis system 100 is usable to monitor the bone ingrowth of the orthopaedic prosthesis 102 over time while the orthopaedic prosthesis 102 is implanted in the patient. To do so, the orthopaedic prosthesis 102 includes a securement monitoring circuit 110, which may be powered by the external power supply 106 (or via an internal power source) to cause the securement monitoring circuit 110 to transmit force sensor data produced by a force sensor 118 of the securement monitoring circuit 110. As discussed in more detail below, the force sensor data is indicative of an amount of force applied to the stem of the orthopaedic prosthesis 102 received in the medullary canal of the patient. However, the amount of force applied to the stem is dependent upon the present amount of bone ingrowth of the orthopaedic prosthesis 102. That is, the loading of the stem of the orthopaedic prosthesis 102 (i.e., the amount of force applied to the stem) while the patient performs an activity of daily living (e.g., walking, climbing stairs, etc.) is typically greatest immediately after implantation of the orthopaedic prosthesis 102 and decreases over time as the bone of the patient grows into the orthopaedic prosthesis 102. As such, the orthopaedic surgeon may monitor the force sensor data over time to determine whether the orthopaedic prosthesis 102 has experienced sufficient bone ingrowth and, if not, perform a surgical or non-surgical intervention to correct the securement of the orthopaedic prosthesis 102.

To facilitate the monitoring of the bone ingrowth of the orthopaedic prosthesis 102, the external data communication device 104 is configured to receive the force sensor data transmitted by the securement monitoring circuit 110 of the orthopaedic prosthesis 102 and display or generate indicia of the amount of, or sufficiency of, the bone ingrowth of the orthopaedic prosthesis 102. The indicia of bone ingrowth may be embodied as the force sensor data directly or may be embodied as other data derived from the force senor data, such as data that is a reduction or simplification of the force sensor data (e.g., a simple indication of whether the bone ingrowth satisfies a reference threshold value). Regardless, as discussed above, the orthopaedic surgeon may monitor the indicia of bone ingrowth over time to determine whether the orthopaedic prosthesis 102 has experienced sufficient bone ingrowth.

The orthopaedic prosthesis 102 may be embodied as any type of orthopaedic prosthesis configured to replace a partial or complete joint of a patient and including the securement monitoring circuit 110. For example, and as discussed in more detail below in regard to FIGS. 2-6, the orthopaedic prosthesis 102 may be embodied as an tibial knee component, a femoral stem component, an acetabular cup component, or other orthopaedic prosthesis.

As shown in FIG. 1, the orthopaedic prosthesis 102 includes the securement monitoring circuit 110, which may be embodied as any type of circuit or collection of components capable of producing and transmitting force sensor data indicative of an amount of force applied to a stem of the orthopaedic prosthesis 102. In the illustrative embodiment, the securement monitoring circuit 110 includes a power circuit 112, a processing circuit 114, a communication circuit 116, and the force sensor 118. Although illustrated as separate electrical circuits or components in FIG. 1, it should be appreciated that some or all of the circuits/components of the securement monitoring circuit 110 may be embodied as a single circuit such as an integrated circuit, an embedded system, a field-programmable-array (FPGA), a system-on-a-chip (SOC), or other integrated system or device.

The power circuit 112 is configured to provide power to the processing circuit 114 and other components of the securement monitoring circuit 110. In the illustrative embodiments, the power circuit 112 is embodied as a remotely-powered power circuit configured to receive power from the external power supply 106. For example, the power circuit 112 may be embodied as an acoustically- or inductively-powered power circuit 112 that is configured to be acoustically or inductively coupled with the external power supply 106 to receive power therefrom. In such embodiments, the power circuit 112 may include additional circuits or components to prepare the received power for delivery to the circuits of the securement monitoring circuit 110, such as filtering or conditioning circuits, step-down or step-up circuits, regulation circuits, and/or the like. Of course, in other embodiments, the power circuit 112 may include a local or on-board power supply, such as a battery.

The processing circuit 114 may be embodied as any type of controller, processor, or other processing circuitry capable of performing the functions described herein. For example, the processing circuit 114 may be embodied as a microcontroller, a digital signal processor, a single or multi-core processor(s), discrete compute circuitry, or other processor or processing/controlling circuitry. For example, as shown in FIG. 1, the processing circuit 114 may include a processor 120 and a memory 122. The processor 120 may be embodied as any type of processor capable of performing the functions described herein. For example, the processor 120 may be embodied as a single or multi-core processor(s), a digital signal processor, a microcontroller, discrete compute circuitry, other processor or processing/controlling circuitry. Similarly, the memory 122 may be embodied as any type of volatile and/or non-volatile memory or data storage capable of storing data, such as the force sensor data produced by the force sensor 118. Of course, the processing circuit 114 may include additional or other components commonly found in a compute device or circuit, such as an input/output subsystem, additional memory, accelerator circuitry, encryption/description circuit, and/or other components.

The communication circuit 116 is configured to communicate with external devices such as the external data communication device 104 and/or other remote devices. The communication circuit 116 may be embodied as any type of communication circuit or device capable of facilitating communications between the securement monitoring circuit 110 and the external data communication device 104. To do so, the communication circuit 116 may be configured to use any suitable wireless communication protocol (e.g., Bluetooth®, Wi-Fi®, etc.) to effect such communication.

The force sensor 118 may be embodied as any type of force sensor capable of producing sensor data indicative of an amount of force applied to or otherwise exerted on a stem of the orthopaedic prosthesis 102 while the orthopaedic prosthesis 102 is implanted in a patient. For example, in the illustrative embodiment, the force sensor 118 is embodied as a piezoelectric force sensor, which utilizes the piezoelectric effect to convert a sensed change in force to an electrical charge, which may be associated with a measurement of force. Additionally, the illustrative force sensor 118 is a three-axis force sensor capable of sensing forces in three different axes. However, a single or dual axis force sensor may be used in other embodiments. Additionally, in other embodiments, other types of force sensors may be used such as strain gauges, load cells, and the like.

The force sensor 118 is coupled to a stem of the orthopaedic prosthesis 102 to facilitate the sensing of forces applied to the stem. The force sensor 118 may be secured in one of several locations on the stem of the orthopaedic prosthesis 102 depending on the type of prosthesis. For example, in the embodiment shown in FIG. 2, the orthopaedic prosthesis 102 is embodied as a tibial knee component 200 having a tibial tray 202 and a stem 204 extending from a bottom side 206 of the tibial tray 202. The stem 204 includes a proximal end 210 attached, integrally or separately, to the bottom side 206 of the tibial tray 202 and a distal end 212 opposite the proximal end. In the illustrative embodiment, the force sensor 118 is shaped to form a distal tip 214 of the distal end 212 of the stem 204. The force sensor 118 may be integrally formed with the stem 204 or form a separate component that is attached to the distal end 212 of the stem 204 to form the distal tip 214.

The tibial tray 202 and the stem 204 are formed from an implant-grade metallic material such as, for example, stainless steel or cobalt chromium. The illustrative tibial knee component 200 is embodied as a cementless orthopaedic prosthesis and, as such, includes a porous-metal coating 220 disposed on an outer surface 222 of the stem 204. The porous-metal coating 220 covers the force sensor 118, but is shown partially removed in FIG. 2 to illustrate the location of the force sensor 118. The porous-metal coating 220 may be embodied as any type of porous-metal coating capable of facilitating bone ingrowth therein. For example, in some embodiments, the porous-metal coating may be embodied as a separately-applied coating such as Porocoat® Porous Coating, which is commercially available from DePuy Synthes of Warsaw, Ind. Alternatively, the porous-metal coating 220 may be disposed on the metallic stem 204 by virtue of being additively manufactured contemporaneously with the metallic stem 204 so as to create a common, monolithic component of the two metal structures.

In use, as discussed above, the force sensor 118 is configured to sense forces applied to the stem 204 while the orthopaedic prosthesis 102, 200 is implanted in the patient. Such forces are indicative of a loading of the stem 204, which may be greatest when the orthopaedic prosthesis 102, 200 is initially implanted into the patient's bone but generally decreases over time as the patient's bone grows into the porous-metal coating 220. As such, decreasing force sensor data produced by the force sensor 118 is generally indicative that bone ingrowth into the porous-metal coating 220 is occurring and the orthopaedic prosthesis 102, 200 is becoming secured to the patient's bone.

Figure 3:
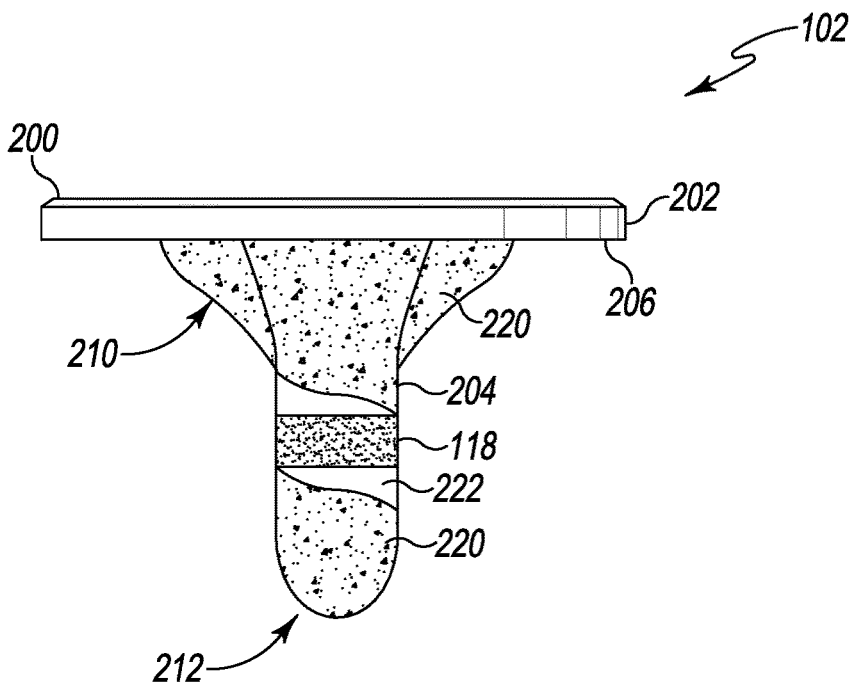
FIG. 3 is an elevation view of another embodiment of the tibial knee component of FIG. 2.

In other embodiments, as shown in FIG. 3, the force sensor 118 may be embodied as an annular force sensor coupled to the stem 204 of the tibial knee component 200 between the proximal end 210 and the distal end 212. The force sensor 118 may be integrally formed with the stem 204 or form a separate component that is attached to the outer surface 222 of the stem 204. In either case, the porous-metal coating 220 covers the force sensor 118, but is shown in FIG. 3 partially removed to illustrate the location of the force sensor 118. Additionally, as discussed above, the force sensor 118 is configured to sense forces applied to the stem 204 while the orthopaedic prosthesis 102, 200 is implanted in the patient.

Figure 4:
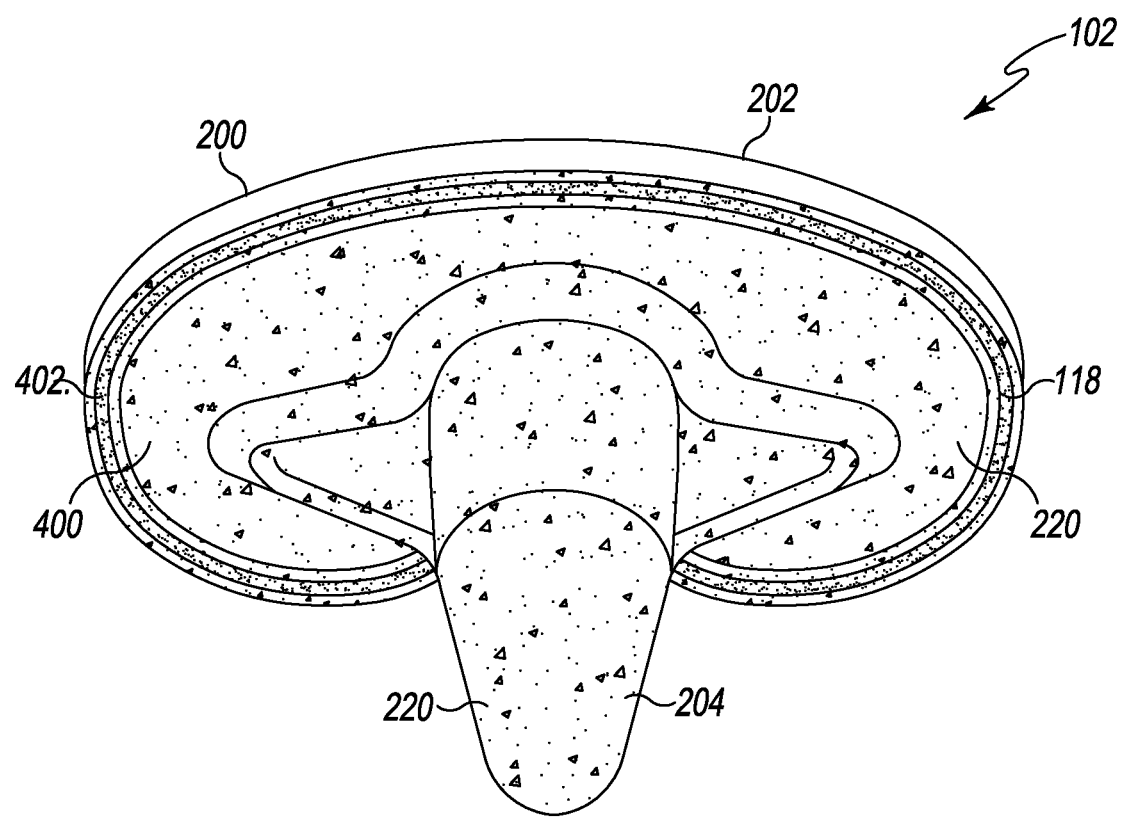
FIG. 4 is an bottom perspective view of yet another embodiment of the tibial knee component of FIG. 2.

In some embodiments, the force sensor 118 may be incorporated into other features of the tibial knee component 200 than the stem 204. For example, as shown in FIG. 4, the force sensor 118 may be embodied as an annular force sensor embedded in an inferior or bottom side 400 of the tibial tray 202 of the tibial knee component 200. For example, the force sensor 118 may be secured into a groove defined in an outer lip 402 of the inferior side 400. In such embodiments, the force sensor 118 is configured to sense forces applied to the stem 204 while the orthopaedic prosthesis 102, 200 is implanted in the patient as discussed above.

Figure 5:
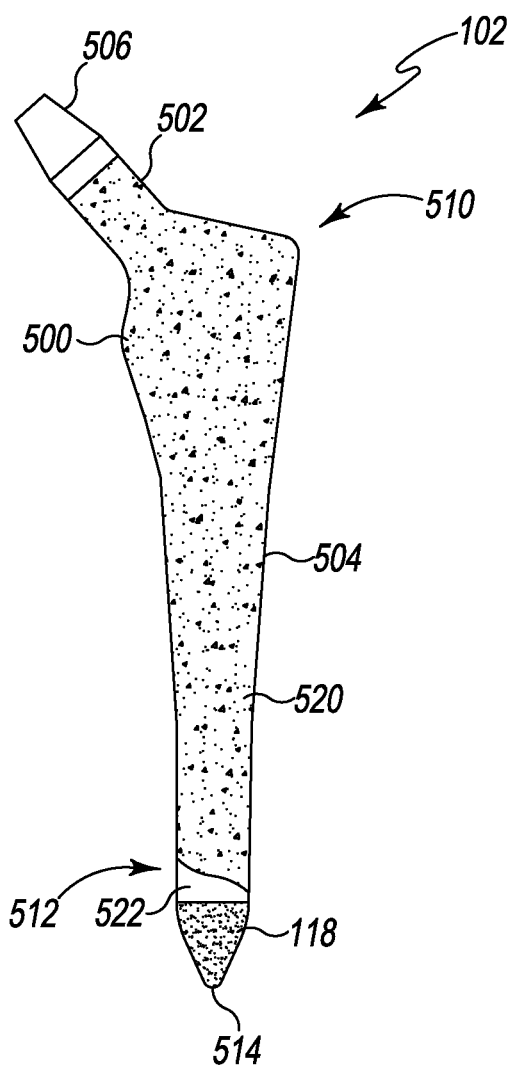
FIG. 5 is an elevation view of the orthopaedic prosthesis of FIG. 1 embodied as a femoral stem component and having a force sensor incorporated therewith.
Figure 6:
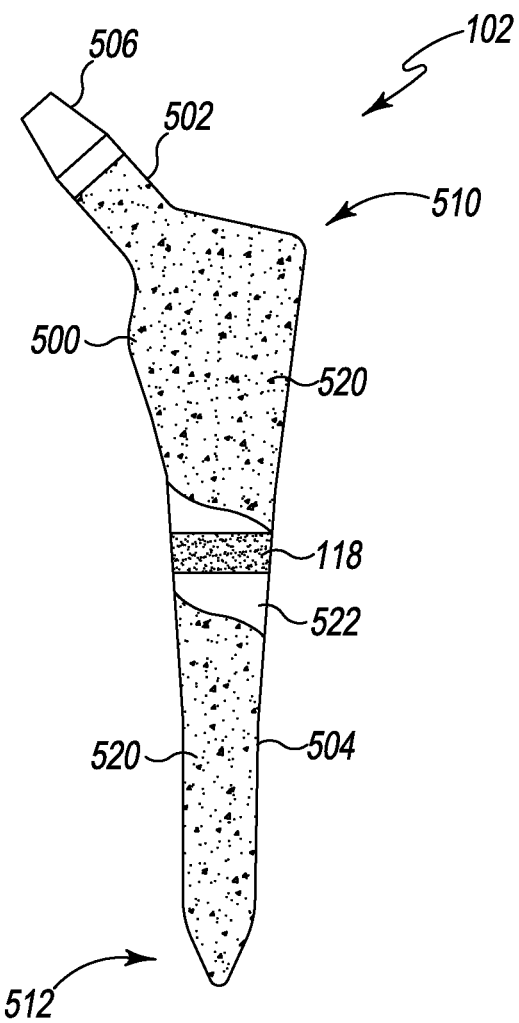
FIG. 6 is an elevation view of another embodiment of the femoral stem component of FIG. 5.

Referring now to FIGS. 5 and 6, in other embodiments, the orthopaedic prosthesis 102 may be embodied as a femoral stem component 500 having a neck 502 and a stem 504 extending distally from the neck 502. The neck 502 illustratively includes a trunnion 506, which is configured to engage a corresponding femoral head component (not shown) to form a tapered lock. The stem 504 includes a proximal end 510 from which the neck 502 extends and a distal end 512 opposite the proximal end 510. In the illustrative embodiment, the force sensor 118 is shaped to form a distal tip 514 of the distal end 512 of the stem 504. Similar to the tibial knee component 200 discussed above in regard to FIG. 2, the force sensor 118 may be integrally formed with the stem 504 or form a separate component that is attached to the distal end 512 of the stem 504 to form the distal tip 514.

Similar to the tibial knee component 200, the femoral stem component 500 is formed from a metallic material such as, for example, stainless steel or cobalt chromium. The illustrative femoral stem component 500 is embodied as a cementless orthopaedic prosthesis and includes a porous-metal coating 520 disposed on an outer surface 522 of the stem 204. The porous-metal coating 520 covers the force sensor 118, but is shown partially removed in FIG. 5 to illustrate the location of the force sensor 118. The porous-metal coating 520 is similar to the porous-metal coating 220 described above and may be embodied as any type of porous-metal coating capable of facilitating bone ingrowth therein. For example, in some embodiments, the porous-metal coating 520 may be embodied as a separately-applied coating such as Porocoat® Porous Coating, which is commercially available from DePuy Synthes of Warsaw, Ind. Alternatively, the porous-metal coating 520 may be disposed on the metallic stem 504 by virtue of being additively manufactured contemporaneously with the metallic stem 504 so as to create a common, monolithic component of the two metal structures.

In use, as discussed above, the force sensor 118 is configured to sense forces applied to the stem 504 while the orthopaedic prosthesis 102, 500 is implanted in the patient. Such forces are indicative of a loading of the stem 504, which may be greatest when the orthopaedic prosthesis 102, 500 is initially implanted into the patient's bone but generally decreases over time as the patient's bone grows into the porous-metal coating 520. As such, decreasing force sensor data produced by the force sensor 118 is generally indicative that bone ingrowth into the porous-metal coating 520 is occurring and the orthopaedic prosthesis 102, 500 is becoming secured to the patient's bone.

In other embodiments, as shown in FIG. 5, the force sensor 118 may be embodied as an annular force sensor coupled to the stem 504 of the femoral stem component 500 between the proximal end 510 and the distal end 512. The force sensor 118 may be integrally formed with the stem 504 or form a separate component that is attached to the outer surface 522 of the stem 504. In either case, the porous-metal coating 520 covers the force sensor 118, but is shown in FIG. 6 partially removed to illustrate the location of the force sensor 118. Additionally, as discussed above, the force sensor 118 is configured to sense forces applied to the stem 504 while the orthopaedic prosthesis 102, 500 is implanted in the patient.

Figure 7:
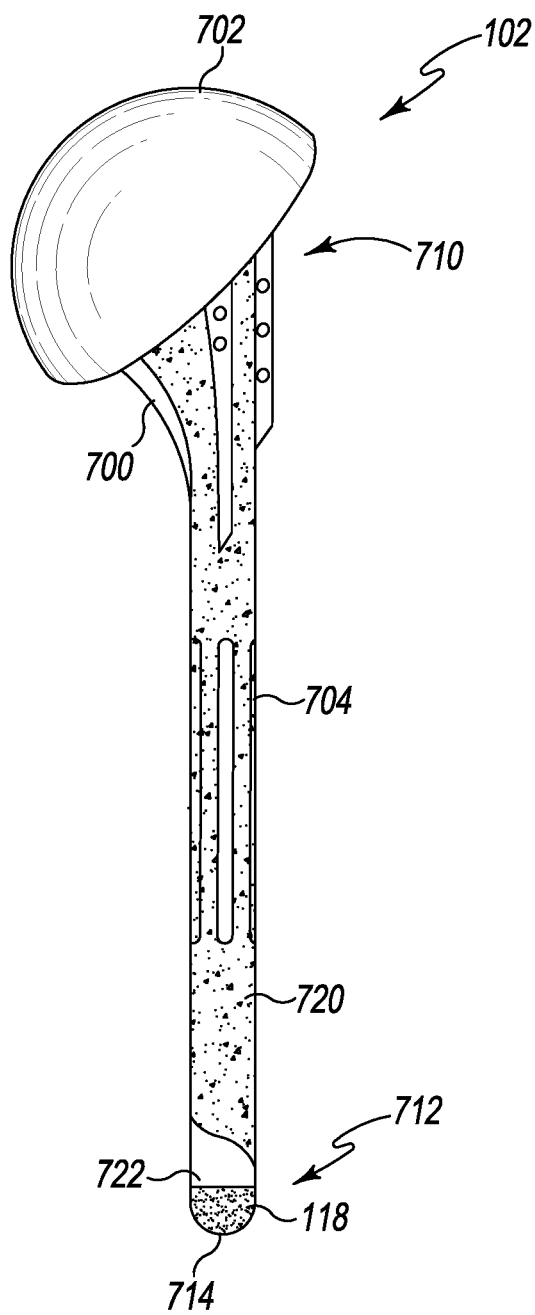
FIG. 7 is an elevation view of the orthopaedic prosthesis of FIG. 1 embodied as a humeral component and having a force sensor incorporated therewith.
Figure 8:
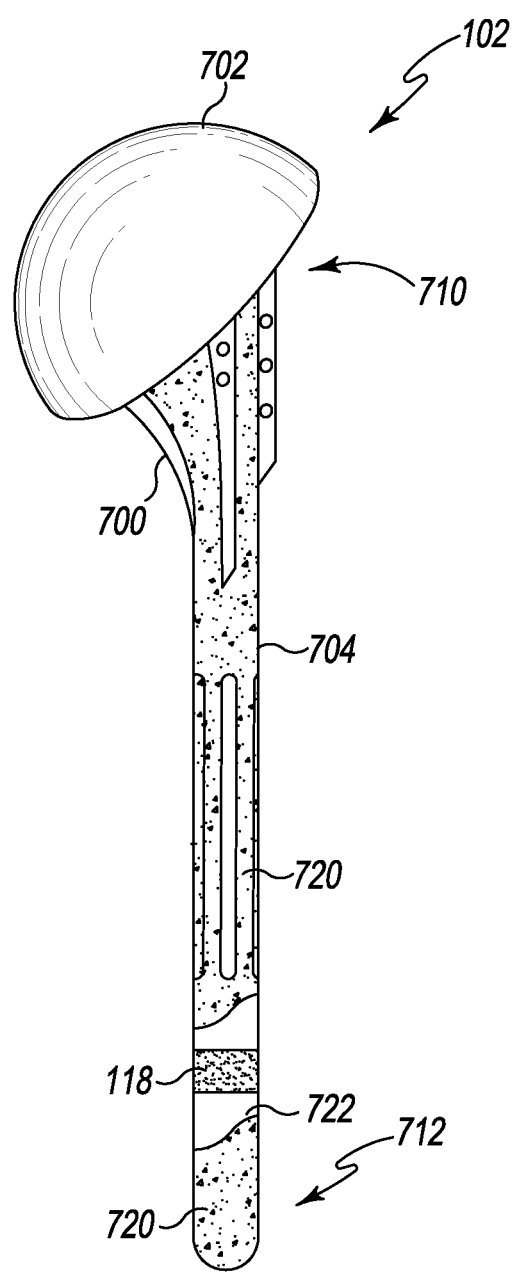
FIG. 8 is an elevation view of another embodiment of the humeral component of FIG. 7.

Referring now to FIGS. 7 and 8, in other embodiments, the orthopaedic prosthesis 102 may be embodied as a humeral component 700 having a prosthetic humeral head 702 and a stem 704 extending distally from the humeral head 702. The humeral head 702 is hemi-spherical in shape and configured to articulate on a corresponding bearing surface of a natural or prosthetic glenoid cavity of a patient. The stem 704 includes a proximal end 710 attached to or formed with the humeral head 702 and a distal end 712 opposite the proximal end 710. In the illustrative embodiment, the force sensor 118 is shaped to form a distal tip 714 of the distal end 712 of the stem 704. Similar to the tibial knee component 200 discussed in regard to FIG. 2, the force sensor 118 may be integrally formed with the stem 704 or form a separate component that is attached to the distal end 712 of the stem 704 to form the distal tip 714.

Similar to the tibial knee component 200, the humeral component 700 is formed from a metallic material such as, for example, stainless steel or cobalt chromium. The illustrative humeral component 700 is embodied as a cementless orthopaedic prosthesis and includes a porous-metal coating 720 disposed on an outer surface 722 of the stem 704. The porous-metal coating 720 covers the force sensor 118, but is shown partially removed in FIG. 7 to illustrate the location of the force sensor 118. The porous-metal coating 720 is similar to the porous-metal coating 220 described above and may be embodied as any type of porous-metal coating capable of facilitating bone ingrowth therein. For example, in some embodiments, the porous-metal coating 720 may be embodied as a separately-applied coating such as Porocoat® Porous Coating, which is commercially available from DePuy Synthes of Warsaw, Ind. Alternatively, the porous-metal coating 720 may be disposed on the stem 704 by virtue of being additively manufactured contemporaneously with the stem 704 so as to create a common, monolithic component of the two metal structures.

In use, as discussed above, the force sensor 118 is configured to sense forces applied to the stem 704 while the orthopaedic prosthesis 102, 700 is implanted in the patient. Such forces are indicative of a loading of the stem 704, which may be greatest when the orthopaedic prosthesis 102, 700 is initially implanted into the patient's bone but generally decreases over time as the patient's bone grows into the porous-metal coating 720. As such, decreasing force sensor data produced by the force sensor 118 is generally indicative that bone ingrowth into the porous-metal coating 720 is occurring and the orthopaedic prosthesis 102, 700 is becoming secured to the patient's bone.

In other embodiments, as shown in FIG. 8, the force sensor 118 may be embodied as an annular force sensor coupled to the stem 704 of the humeral stem component 700 between the proximal end 710 and the distal end 712. The force sensor 118 may be integrally formed with the stem 704 or form a separate component that is attached to the outer surface 722 of the stem 704. In either case, the porous-metal coating 720 covers the force sensor 118, but is shown in FIG. 8 partially removed to illustrate the location of the force sensor 118. Additionally, as discussed above, the force sensor 118 is configured to sense forces applied to the stem 704 while the orthopaedic prosthesis 102, 700 is implanted in the patient.

Referring back to FIG. 1, the external data communication device 104 may be embodied as any type of computer, device, or collection of devices capable of performing various compute or analysis functions and the functions described herein including, but not limited to, a desktop computer, a workstation, a server, a special-built compute device, a mobile compute device, a laptop computer, a tablet computer, or other computer or compute device. In the illustrative embodiment, the external data communication device 104 includes a processor 132, a memory 134, an I/O subsystem 136, a communication circuit 138, and an output device 140. The processor 132 may be embodied as any type of processor capable of performing the functions described herein. For example, the processor 132 may be embodied as a single or multi-core processor(s), a digital signal processor, a microcontroller, discrete compute circuitry, other processor or processing/controlling circuitry. Similarly, the memory 134 may be embodied as any type of volatile and/or non-volatile memory or data storage capable of storing data, such as the force sensor data received from the orthopaedic prosthesis 102. The external data communication device 104 may also include other components commonly found in a compute device, such as a data storage device and various input/output devices (e.g., a keyboard, mouse, display, etc.). Additionally, although illustrated as a single device, it should be understood that in some embodiments, the external data communication device 104 may be formed from multiple computing devices distributed across a network, for example operating in a public or private cloud.

The external data communication device 104 is communicatively coupled to other components of the orthopaedic prosthesis system 100 via the I/O subsystem 136, which may be embodied as circuitry and/or components to facilitate input/output operations with the external data communication device 104 (e.g., with the processor 132 and/or the memory 134) and other components of the orthopaedic prosthesis system 100. For example, the I/O subsystem 136 may be embodied as, or otherwise include, memory controller hubs, input/output control hubs, firmware devices, communication links (i.e., point-to-point links, bus links, wires, cables, light guides, printed circuit board traces, etc.) and/or other components and subsystems to facilitate the input/output operations.

The communication circuit 138 is configured to communicate with external devices such as the securement monitoring circuit 110 of the orthopaedic prosthesis 102 and/or other remote devices. As such, the communication circuit 138 may be embodied as any type of communication circuit or device capable of facilitating communications between the external data communication device 104 and the securement monitoring circuit 110 of the orthopaedic prosthesis 102. To do so, the communication circuit 138 may be configured to use any suitable wireless communication protocol (e.g., Bluetooth®, Wi-Fi®, etc.) to effect such communication.

The output device 140 may be embodied as any type of output device capable of providing a notification or other information to the orthopaedic surgeon or other user. In the illustrative embodiment, the output device 140 is embodied as, or otherwise includes, a display for displaying indicia of bone ingrowth (e.g., force sensor data) to the orthopaedic surgeon during a post-operative examination process as discussed in more detail below, but may be embodied as other types of output devices in other embodiments including, for example, and audible output device.

The external power supply 106 may be embodied as any type of device, circuit, component, or collection thereof, capable of providing power to the power circuit 112 of the securement monitoring circuit 110 of the orthopaedic prosthesis 102 while the orthopaedic prosthesis 102 is implanted in a patient. For example, the external power supply 106 may be configured to acoustically or inductively couple with the power circuit 112 to transfer an amount of power to the securement monitoring circuit 110.

Figure 9A:
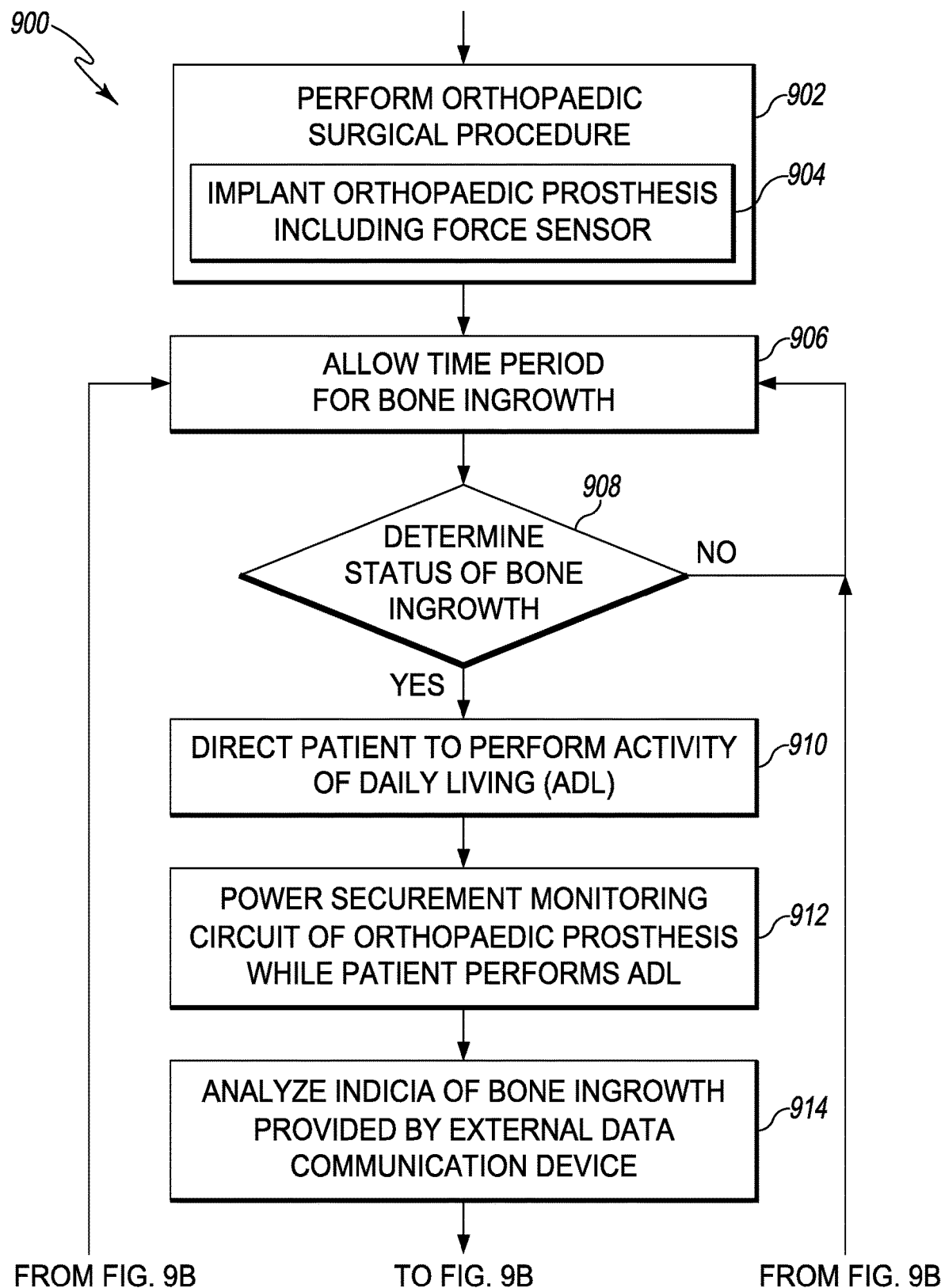
FIGS. 9A and 9B are a flow diagram of an embodiment of a surgical method for monitoring bone ingrowth in the orthopaedic prosthesis of FIG. 1 while implanted in a patient.
Figure 9B:
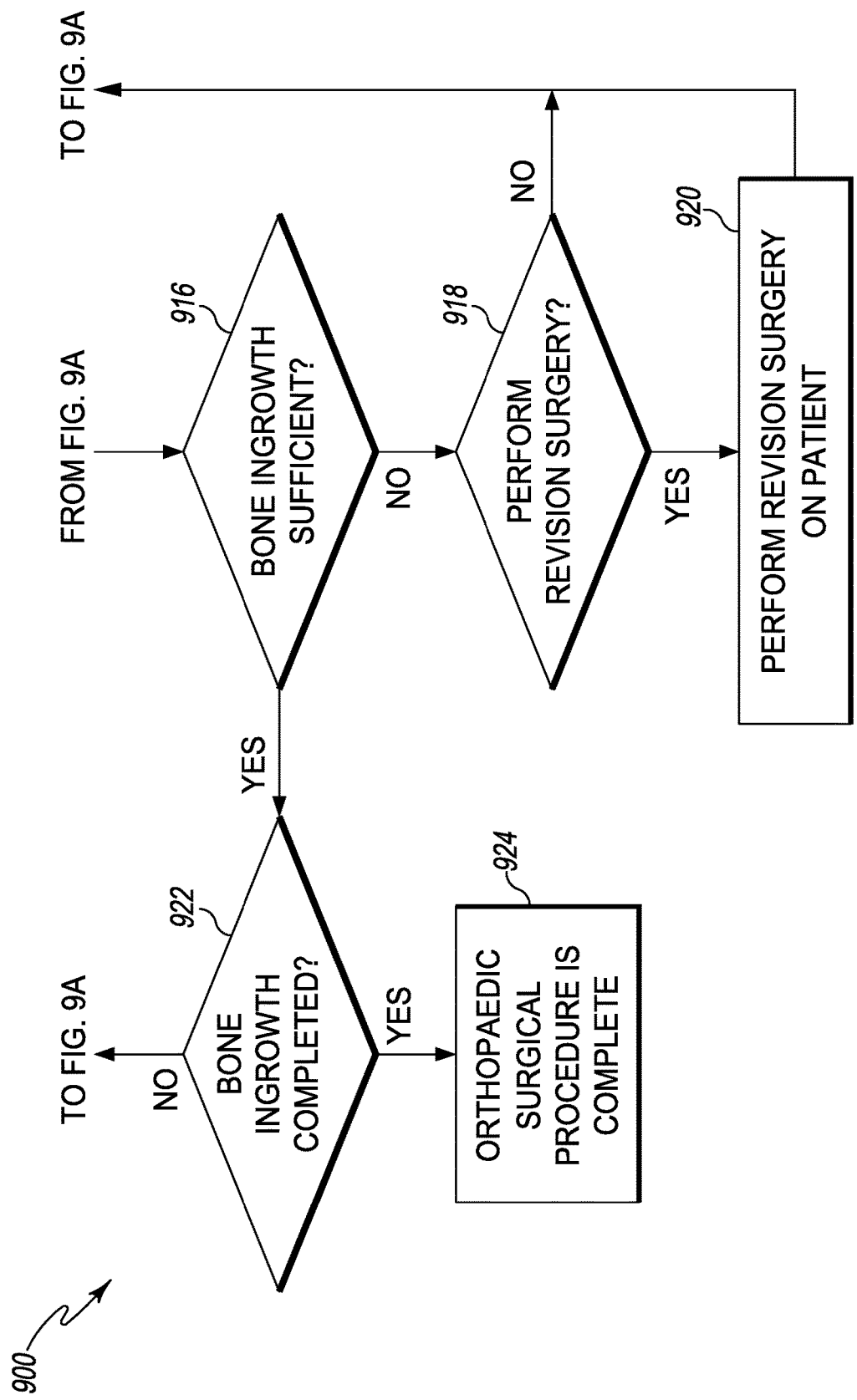

Referring now to FIGS. 9A and 9B, during use, an orthopaedic surgeon may perform a surgical method 900 using the orthopaedic prosthesis system 100. The method 900 begins with block 902 in which the orthopaedic surgeon performs an orthopaedic surgical procedure, such as a primary joint arthroplasty procedure, on a patient, which includes implanting the orthopaedic prosthesis 102 as shown in block 904. The orthopaedic surgeon may use any appropriate surgical technique and associated surgical instruments to perform the orthopaedic surgical procedure depending on, for example, the particular type of prosthesis of the orthopaedic prosthesis 102 (e.g., whether the orthopaedic prosthesis is a tibial knee component, a femoral stem component, etc.).

In block 906, the orthopaedic surgeon allows some amount of time for the patient's bone to grow into the porous-metal coating 220, 520 of the orthopaedic prosthesis 102. For example, the orthopedic surgeon may allow minutes, hours, days, weeks, months, or years to pass. The particular length of the time period of block 906 may be based on several factors such as the length of time since the orthopaedic surgical procedure of block 902 (e.g., the length of time of block 906 may grow longer after each visit with the orthopaedic surgeon), the particular joint of the patient on which the orthopaedic surgical procedure was performed, and/or other criteria.

In block 908, the orthopaedic surgeon decides whether to determine the status of bone ingrowth of the orthopaedic prosthesis 102 during a subsequent post-operative examination procedure of the patient. It should be appreciated that the orthopaedic surgeon may not determine the status of bone ingrowth during every post-operative examination of the patient and/or may determine the status of the bone ingrowth based on other criteria than the amount of elapsed time between the original orthopaedic surgery procedure of block 902 or the last post-operative examination such as, for example, if the patient is experiencing trouble with the orthopaedic prosthesis 102.

If the orthopaedic surgeon decides not to determine the status of the bone ingrowth of the orthopaedic prosthesis 102 in block 908, the method 900 loops back to block 906 in which the orthopaedic surgeon may allow additional time for bone ingrowth. If, however, the orthopaedic surgeon decides to proceed with the determination of bone ingrowth, the method 900 advances to block 910 in which the orthopaedic surgeon directs the patient to perform an activity of daily living (ADL). The particular activity of daily living performed by the patient may vary based on the abilities of the patient, the particular joint of the patient that was replaced, and/or other factors.

In block 912, while the patient is performing the activity of daily living, the orthopaedic surgeon powers the securement monitoring circuit 110 of the orthopaedic prosthesis 102. To do so, the orthopaedic surgeon may utilize the external power supply 106 to transfer an amount of power to the power circuit 112 of the securement monitoring circuit 110.

Figure 10A:
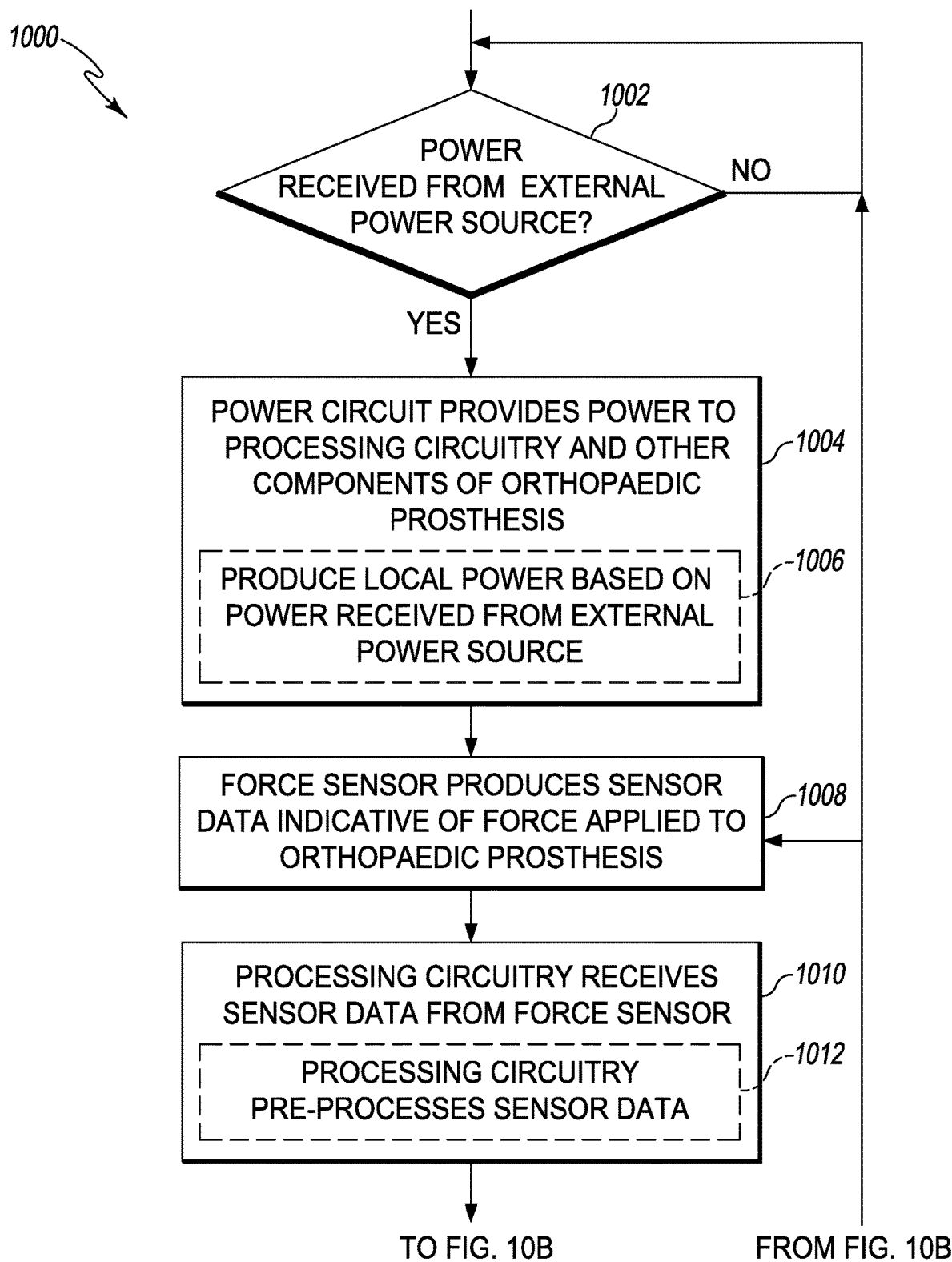
FIGS. 10A and 10B are a flow diagram of an embodiment of a method for communicating force sensor data, which may be executed by a securement monitoring circuit of the orthopaedic prosthesis of FIG. 1.
Figure 10B:
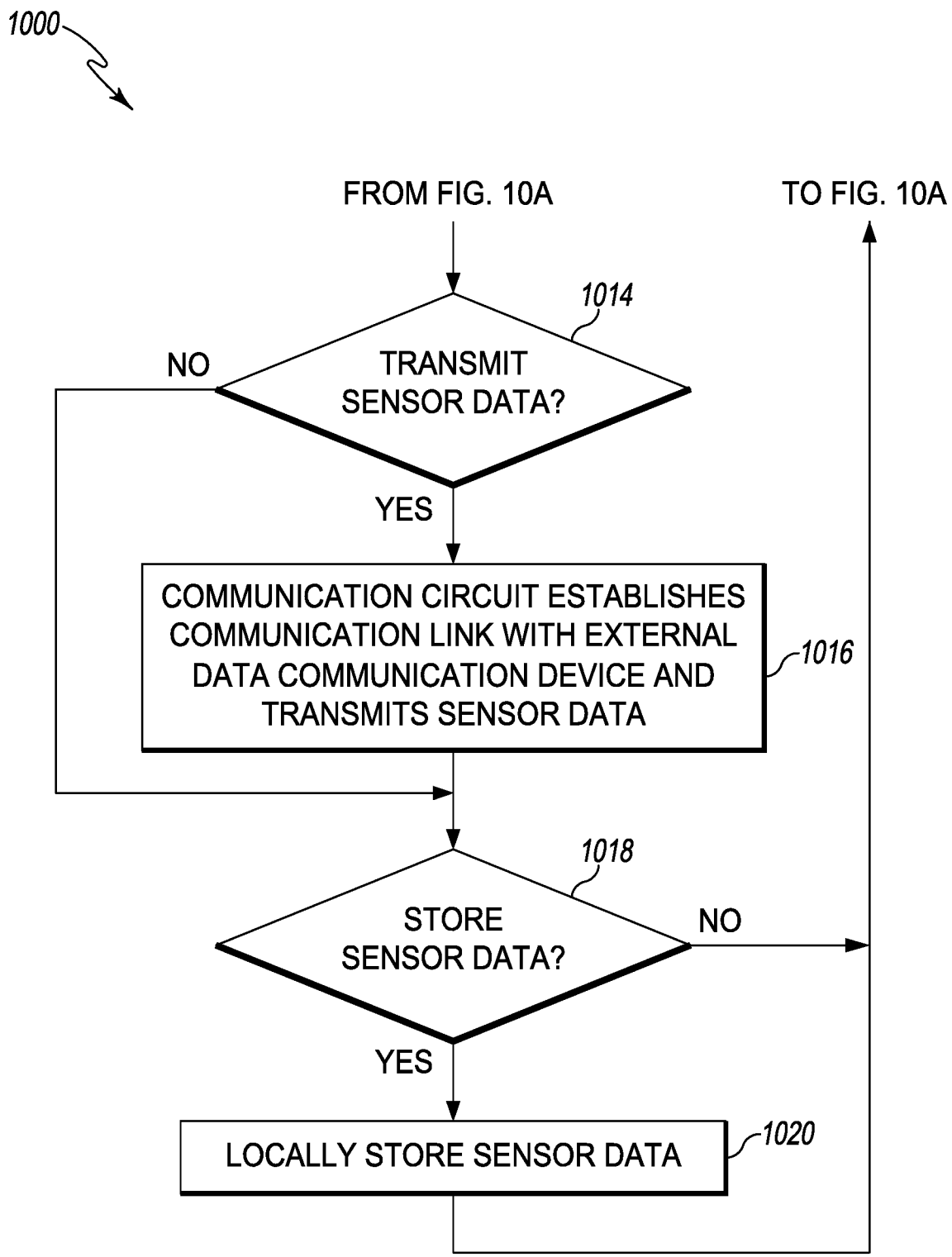

In response to receiving the power from the external power supply 106, the securement monitoring circuit 110 transmits the force sensor data produced by the force sensor 118 to the external data communication device 104. To do so, as shown in FIGS. 10A and 10B, the securement monitoring circuit 110 may execute a method 1000 for communicating force sensor data, which may be embodied, in whole or in part, as a set of instructions executable by the processing circuit 114 or other component(s) of the securement monitoring circuit 110. The method 1000 begins with block 1002 in which the power circuit 112 determines whether power has been received from the external power supply 106. If so, the method 1000 advances to block 1004 in which the power circuit 112 provides power to the processing circuit 114 and other components of the securement monitoring circuit 110. In doing so, in block 1006, the power circuit 112 may perform various processing of the power received from the external power supply 106 such as filtering, transforming, conditioning, regulating, etc., to generate a local power suitable for powering the processing circuit 114 and other components of the securement monitoring circuit 110. Of course, in other embodiments as discussed above, the power circuit 112 of the securement monitoring circuit 110 may be embodied as an independent power source, such as a battery; and in such embodiments, the power circuit 112 may perform the functionality of block 1004 without receiving power form the external power supply in block 1002.

Regardless, in block 1008, the force sensor 118 produces force sensor data, which is indicative of an amount of force applied to the stem 204, 504, 704 or other feature of the orthopaedic prosthesis 102. It should be appreciated that because the securement monitoring circuit 110 is powered while the patient is performing the activity of daily living, the force sensor data produced by that force sensor 118 is indicative of force exhibited on the stem 204, 504, 704 or other feature while the patient performs the activity of daily living (e.g., the force applied to the stem 204, 504, 704 or other feature while the patient walks, climbs stairs, etc.).

In block 1010, the processing circuit 114 receives the force sensor data produced by the force sensor 118 and, in block 1012, may perform some amount of pre-processing of the force sensor data in some embodiments. For example, the processing circuit 114 may be configured to filter or condition the force sensor data. Additionally, in some embodiments, the processing circuit 114 may be configured to process the force sensor data to generate bone ingrowth data indicative of the bone ingrowth of the orthopaedic prosthesis 102, which may be embodied as a reduction or simplification of the force sensor data. For example, the processing circuit 114 may compare the force sensor data to a reference threshold force value and generate an indication (e.g., a binary indication) of whether the bone ingrowth is sufficient or not.

Regardless, in block 1014 of FIG. 10B, the securement monitoring circuit 110 determines whether to transmit the force sensor data (and/or the bone ingrowth data if generated) to the external data communication device 104. If so, the communication circuit 116 of the securement monitoring circuit 110 establishes a communication link with the communication circuit 138 of the external data communication device 104 and transmits the force sensor data (and/or the bone ingrowth data) to the external data communication device 104 in block 1016.

If the securement monitoring circuit 110 determines not to transfer the force sensor data in block 1014 or after the securement monitoring circuit 110 transfers the force sensor data in block 1016, the securement monitoring circuit 110 determines whether to locally store the force sensor data in block 1018. The securement monitoring circuit 110 may locally store the force sensor data to, for example, facilitate the transfer of batches of force sensor data in block 1016. If the force sensor data is to be locally stored, the securement monitoring circuit 110 stores the force sensor data produced by the force sensor 118 in the memory 122 or other data storage of the securement monitoring circuit 110 in block 1020. After the force sensor data has been stored or if the force sensor data is not locally stored, the method 1000 loops back to block 1002 in which power circuit 112 determines whether power has been received from the external power supply 106.

Figure 11A:
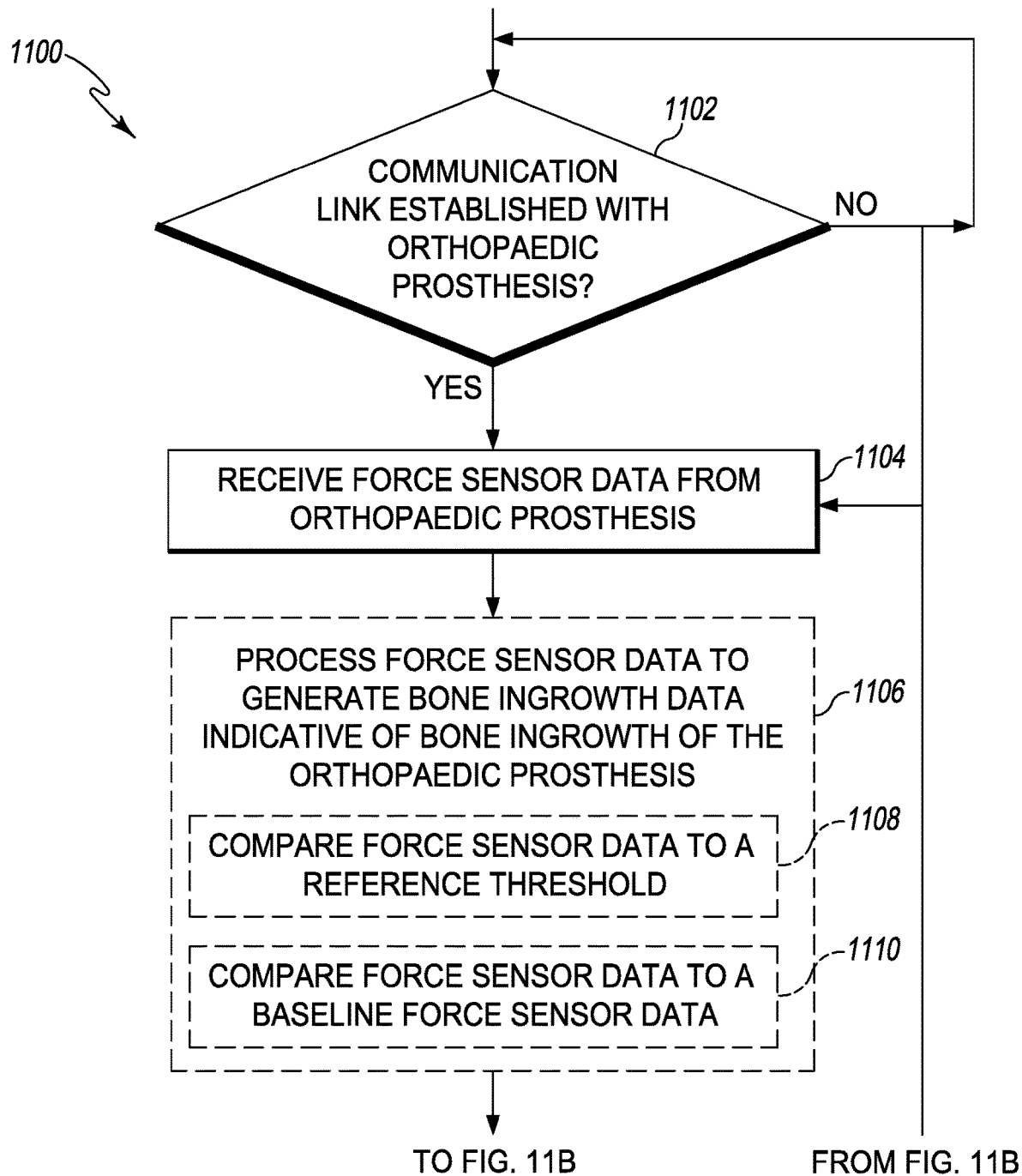
FIGS. 11A and 11B is a flow diagram of an embodiment of a method for managing bone ingrowth data, which may be executed by an external data communication device of the system of FIG. 1.
Figure 11B:
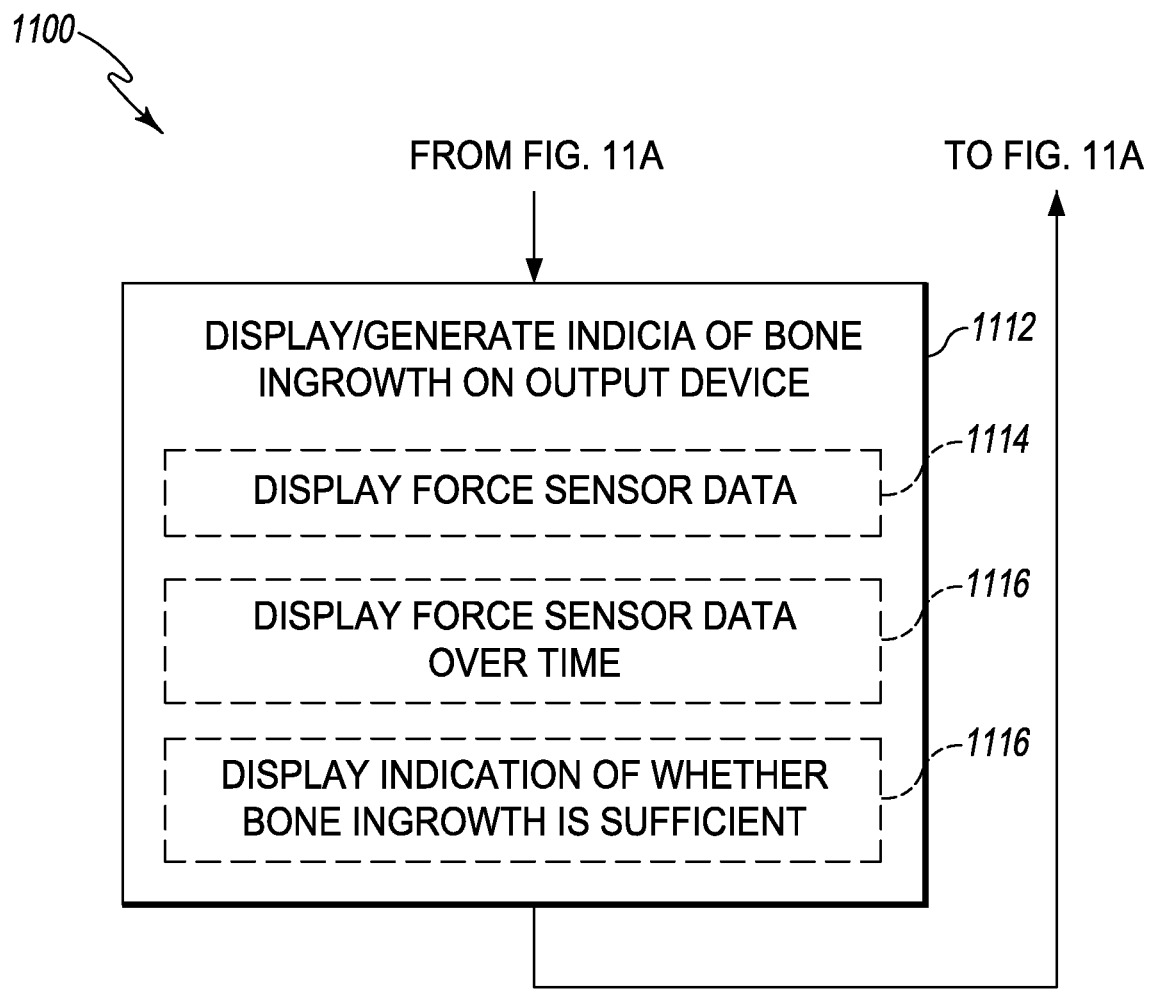

Referring back to block 912 of FIG. 9A, after the orthopaedic surgeon has provided power to the orthopaedic prosthesis 102 to cause the securement monitoring circuit 110 to transmit the force sensor data (and/or bone ingrowth data if any) to the external data communication device 104, the method 900 advances to block 914. In block 914, the orthopaedic surgeon analyzes indicia of the patient's bone ingrowth of the orthopaedic prosthesis 102 provided by the external data communication device 104. That is, as discussed above, the external data communication device 104 is configured to receive the force sensor data from the orthopaedic prosthesis 102 and provide indicia of the bone ingrowth of the orthopaedic prosthesis 102 based on the received force sensor data. To do so, as shown in FIGS. 11A and 11B, the external data communication device 104 may execute a method 1100 for managing bone ingrowth data, which may be embodied, in whole or in part, as a set of instructions executable by the processor 132 and/or other component(s) of the external data communication device 104.

The method 1100 begins with block 1102 in which the external data communication device 104 determines whether a communication link has been established with the securement monitoring circuit 110. As discussed above in regard to block 1016 of method 1000, the communication circuit 116 of the securement monitoring circuit 110 of the orthopaedic prosthesis 102 may establish a communication link with the communication circuit 138 of the external data communication device 104 when force sensor data (or bone ingrowth data) is to be transmitted.

If a communication link has been established with the orthopaedic prosthesis 102 in block 1102, the method 1100 advances to block 1104 in which the external data communication device 104 receives the forces sensor data (and/or bone ingrowth data if any) from the securement monitoring circuit 110. Subsequently, in some embodiments in block 1106, the external data communication device 104 may process the force sensor data to generate bone ingrowth data indicative of bone ingrowth of the orthopaedic prosthesis 102. Similar to the bone ingrowth data optionally generated by the securement monitoring circuit 110, the bone ingrowth data generated by the external data communication device 104 may be embodied as a reduction or simplification of the force sensor data. For example, in block 1108, the external data communication device 104 may compare the force sensor data to a reference threshold value to produce an indication (e.g., a binary indication) of whether the bone ingrowth is sufficient or not. In some embodiments, the reference threshold value may be set to a maximum force value selected to indicate that a force measurement value equal to or less than the reference threshold value is indicative of sufficient bone ingrowth of the orthopaedic prosthesis 102. In some embodiments, the reference threshold value may be selected to be zero or near-zero Newtons. Of course, in other embodiments, other maximum force measurement values may be selected as the reference threshold value. Additionally, in some embodiments, the external data communication device 104 may compare the force sensor data to baseline force sensor data obtained during the first or most-recent post-operative examination of the patient in block 1110.

Figure 12:
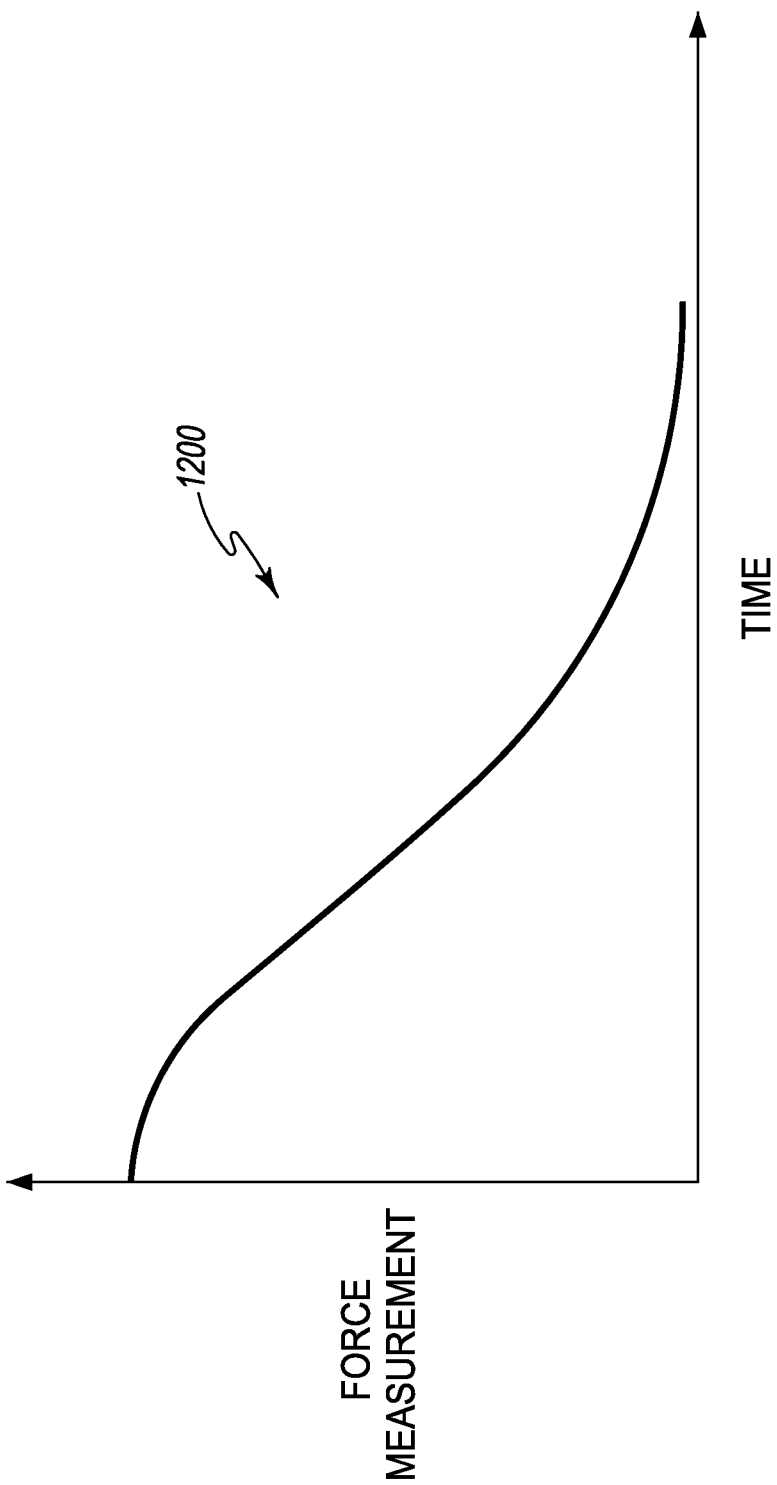
FIG. 12 is an illustrative graph of force sensor data of the orthopaedic prosthesis of FIG. 1 over time.

Subsequently, in block 1112 of FIG. 11B, the external data communication device 104 displays indicia of bone ingrowth on the output device 140 for analysis by the orthopaedic surgeon. To do so, in some embodiments in block 1114, the external data communication device 104 may simply display the force sensor data received from the securement monitoring circuit 110 on the output device 140. Additionally or alternatively, in some embodiments in block 1116, the external data communication device 104 may display the force sensor data over time. For example, as shown in FIG. 12, the external data communication device 104 may display a graph 1200 that charts force measurements versus time, allowing the orthopaedic surgeon to review a historical record of the force sensor data. As shown in the graph 1200, a decrease in the force measurements over time is indicative of proper bone ingrowth of the orthopaedic prosthesis 102. Referring back to FIG. 11B, in still other embodiments, the external data communication device 104 may generate or display a simple indication (e.g., a graphic, a color, an audible tone, etc.) of whether the bone ingrowth is sufficient in block 1118 based on, for example, the processing of the force sensor data performed in block 1106. Regardless, after the external data communication device 104 has displayed or generated the indicia of bone ingrowth of the orthopaedic prosthesis 102 in block 1112, the method 1100 loops back to block 1102 in which the external data communication device 104 determines whether the communication link has been maintained and receives additional force sensor data, if so.

Referring now back to FIG. 9A, after the orthopaedic surgeon analyzes the indicia of bone ingrowth provided by the external data communication device 104 in block 914, the orthopaedic surgeon determines whether the bone ingrowth is sufficient in block 916 of FIG. 9B. The sufficiency of the determined bone ingrowth may be based on several factors including the amount of time since the orthopaedic surgical procedure performed in block 902, the amount of time since the last post-operative examination procedure, the type of orthopaedic prosthesis 102, and/or other factors.

If, in block 916, the orthopaedic surgeon determines that the bone ingrowth is not sufficient, the orthopaedic surgeon may determine whether to perform a revision surgery in block 918. In some cases, the orthopaedic surgeon may determine that surgery is not required or that a non-surgical procedure may be performed to promote bone ingrowth. However, if the orthopaedic surgeon determines that revision surgery is required, the orthopaedic surgeon performs the revision surgery on the patient in block 920. Regardless, in either case, the method 900 loops back to block 906 in which the orthopaedic surgeon allows additional time for bone ingrowth of the orthopaedic prosthesis 102.

Referring back to block 916, if the orthopaedic surgeon determines that the bone ingrowth is sufficient, the orthopaedic surgeon determines whether the bone ingrowth is completed in block 922. That is, in some circumstances, the bone ingrowth may be sufficient for the amount of time since the orthopaedic surgical procedure performed in block 902 but may not yet be completed and may require one or more subsequent post-operative examinations. In such cases, the method 900 loop back to block 906 in which the orthopaedic surgeon allows additional time for bone ingrowth of the orthopaedic prosthesis 102. If, however, the orthopaedic surgeon determines that the bone ingrowth is completed, the orthopaedic surgical procedure is considered to be completed in block 924.

It should be appreciated that while the technologies disclosed herein have been described in regard to a cementless orthopaedic prosthesis, the disclosed technologies are equally applicable to an orthopaedic prosthesis 102 configured to be implanted in a patient using orthopaedic cement. In such cases, the disclosed technologies may be used with a cemented orthopaedic prosthesis 102 to detect loosening of the orthopaedic prosthesis 102 over time. In such embodiments, the orthopaedic surgeon may perform periodic post-operative procedures in which the securement monitoring circuit 110 is powered by the external power supply 106 to cause transmission of the force sensor data to the external data communication device 104. In those embodiments, however, the force sensor data indicative of forces applied to the stem of the cemented orthopaedic prosthesis 102 is indicative of securement of the orthopaedic prosthesis 102 by the orthopaedic cement rather than bone ingrowth. As such, increasing force sensor data may be an indication that the cemented orthopaedic prosthesis 102 is loosening and revision surgery may be required.

While certain illustrative embodiments have been described in detail in the drawings and the foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. An orthopaedic prosthesis for monitoring bone ingrowth, the orthopaedic prosthesis comprising:
   a stem configured to be implanted into a medullary canal of a bone of a patient;
   a porous-metal coating coupled to an external surface of the stem, wherein the porous-metal coating is configured to facilitate ingrowth of the bone of the patient while the orthopaedic prosthesis is implanted into the bone of the patient; and
   a securement monitoring circuit comprising (i) a force sensor coupled to the stem of the orthopaedic prosthesis and positioned underneath the porous-metal coating, wherein the force sensor is configured to produce force sensor data indicative of an amount of force applied to the stem of the orthopaedic prosthesis and wherein the amount of force applied to the stem is dependent on bone ingrowth of the orthopaedic prosthesis, and (ii) a communication circuit configured to transmit the force sensor data to an external data communication device.

2. The orthopaedic prosthesis of claim 1, wherein the orthopaedic prosthesis comprises a tibial component including a tibial tray and the stem, wherein the stem comprises a proximal end coupled to the tibial tray and a distal tip opposite the proximal end, and
   wherein the force sensor comprises an annular force sensor coupled to the stem between the proximal end and the distal tip.

3. The orthopaedic prosthesis of claim 1, wherein the orthopaedic prosthesis comprises a tibial component including a tibial tray and the stem, wherein the stem comprises a proximal end coupled to the tibial tray, and
   wherein the force sensor is shaped to form a distal tip of the stem opposite the proximal end.

4. The orthopaedic prosthesis of claim 1, wherein the orthopaedic prosthesis comprises a femoral component and the stem comprises a proximal end and a distal tip opposite the proximal end, and
   wherein the force sensor comprises an annular force sensor coupled to the stem between the proximal end and the distal tip.

5. The orthopaedic prosthesis of claim 1, wherein the orthopaedic prosthesis comprises a femoral component and the stem comprises a proximal end, and wherein the force sensor is shaped to form the distal tip of the stem opposite the proximal end.

6. The orthopaedic prosthesis of claim 1, wherein the force sensor comprises a 3-axis force sensor.

7. The orthopaedic prosthesis of claim 1, wherein the force sensor comprises a piezoelectric sensor.

8. The orthopaedic prosthesis of claim 1, wherein the securement monitoring circuit further comprises a power circuit to provide power to other electrical components of the securement monitoring circuit, wherein the power circuit is configured to receive power from a power supply external from the orthopaedic prosthesis.

9. The orthopaedic prosthesis of claim 1, wherein the securement monitoring circuit further comprises processing circuitry configured to receive the force sensor data from the force sensor and store the force sensor data in a local memory along with historical force sensor data, and
wherein the communication circuit is further configured to transmit the force sensor data and the historical force sensor data as a batch of force sensor data to the external data communication device.

10. A system for monitoring bone ingrowth of an orthopaedic prosthesis, the system comprising:
an orthopaedic prosthesis having a (i) stem configured to be implanted into a medullary canal of a bone of a patient (ii) a porous-metal coating coupled to an external surface of the stem, wherein the porous-metal coating is configured to facilitate ingrowth of the bone of the patient while the orthopaedic prosthesis is implanted into the bone of the patient; and (iii) a securement monitoring circuit comprising:
a force sensor coupled to the stem of the orthopaedic prosthesis and positioned underneath the porous-metal coating, wherein the force sensor is configured to produce force sensor data indicative of an amount of force applied to the stem of the orthopaedic prosthesis and wherein the amount of force applied to the stem is dependent on bone ingrowth of the orthopaedic prosthesis, and
a communication circuit configured to transmit the force sensor data to an external data communication device; and
an external data communication device comprising (i) a communication circuit configured to communicate with the communication circuit of the orthopaedic prosthesis to receive the force sensor data and (ii) processing circuitry configured to generate, based on the force sensor data, an output on an output device indicative of the bone ingrowth of the orthopaedic prosthesis.

11. The system of claim 10, wherein the orthopaedic prosthesis comprises a tibial component including a tibial tray and the stem, wherein the stem comprises a proximal end coupled to the tibial tray and a distal tip opposite the proximal end, and
wherein the force sensor comprises an annular force sensor coupled to the stem between the proximal end and the distal tip.

12. The system of claim 11, wherein the orthopaedic prosthesis comprises a tibial component including a tibial tray and the stem, wherein the stem comprises a proximal end coupled to the tibial tray, and
wherein the force sensor is shaped to form a distal tip of the stem opposite the proximal end.

13. The system of claim 11, wherein the orthopaedic prosthesis comprises a femoral component and the stem comprises a proximal end and a distal tip opposite the proximal end, and
wherein the force sensor comprises an annular force sensor coupled to the stem between the proximal end and the distal tip.

14. The system of claim 11, wherein the orthopaedic prosthesis comprises a femoral component and the stem comprises a proximal end, and
wherein the force sensor is shaped to form the distal tip of the stem opposite the proximal end.

15. The system of claim 11, wherein the force sensor comprises a 3-axis piezoelectric sensor.

16. The system of claim 10, further comprising an external power supply,
wherein the securement monitoring circuit further comprises a power circuit to provide power to other electrical components of the securement monitoring circuit, and wherein the external power supply is configured to provide power to the power circuit of the securement monitoring circuit while the orthopaedic prosthesis is implanted into the bone of the patient.

* * * * *